(12) United States Patent
Golzar et al.

(10) Patent No.: US 10,543,344 B2
(45) Date of Patent: Jan. 28, 2020

(54) DOUBLE-ENDED WIRE GUIDE AND METHOD OF USE THEREOF

(71) Applicant: Jaafer Golzar, Orland Park, IL (US)

(72) Inventors: Jaafer Golzar, Orland Park, IL (US); Nathan W. Hecht, Bloomington, IN (US)

(*) Notice: Subject to any disclaimer, the term of this patent is extended or adjusted under 35 U.S.C. 154(b) by 387 days.

(21) Appl. No.: 14/823,089

(22) Filed: Aug. 11, 2015

(65) Prior Publication Data

US 2016/0045716 A1 Feb. 18, 2016

Related U.S. Application Data

(60) Provisional application No. 62/037,757, filed on Aug. 15, 2014.

(51) Int. Cl.
| | | |
|---|---|---|
| *A61M 25/09* | (2006.01) | |
| *A61L 31/18* | (2006.01) | |
| *A61L 31/02* | (2006.01) | |
| *A61L 31/10* | (2006.01) | |

(52) U.S. Cl.
CPC ........... *A61M 25/09* (2013.01); *A61L 31/022* (2013.01); *A61L 31/10* (2013.01); *A61L 31/18* (2013.01); *A61M 25/09041* (2013.01); *A61L 2400/10* (2013.01); *A61M 2025/09133* (2013.01); *A61M 2025/09183* (2013.01)

(58) Field of Classification Search
None
See application file for complete search history.

(56) References Cited

U.S. PATENT DOCUMENTS

| | | |
|---|---|---|
| 5,122,136 A | 6/1992 | Gugliemi et al. |
| 5,133,364 A | 7/1992 | Palermo et al. |
| 5,195,978 A | 3/1993 | Schiffer |
| 5,368,595 A | 11/1994 | Lewis |
| 5,423,829 A | 6/1995 | Pham et al. |
| 5,441,055 A | 8/1995 | Ales et al. |
| 5,511,559 A | 4/1996 | Vance |
| 5,569,245 A | 10/1996 | Gugliemi et al. |
| 5,607,406 A | 3/1997 | Hernandez et al. |
| 5,776,079 A | 7/1998 | Cope et al. |
| 5,813,405 A | 9/1998 | Montano, Jr. et al. |
| 5,890,571 A | 4/1999 | Sadow |
| 5,941,888 A | 8/1999 | Wallace et al. |
| 5,964,797 A | 10/1999 | Ho |
| 6,019,757 A | 2/2000 | Scheldrup |
| 6,022,369 A | 2/2000 | Jacobsen et al. |
| 6,123,714 A | 9/2000 | Gia et al. |
| 6,296,622 B1 | 10/2001 | Kurz et al. |
| 6,328,702 B1 | 12/2001 | Cornelius |
| 6,346,091 B1 | 2/2002 | Jacobsen et al. |
| 6,488,637 B1 | 12/2002 | Eder et al. |
| 6,682,493 B2 | 1/2004 | Mirigian |
| 6,911,016 B2 | 6/2005 | Balzum et al. |
| 7,273,486 B2 | 9/2007 | Coyle et al. |

(Continued)

*Primary Examiner* — Sean P Dougherty
*Assistant Examiner* — Benjamin S Melhus
(74) *Attorney, Agent, or Firm* — Cherskov Flaynik & Gurda, LLC

(57) ABSTRACT

The present invention generally relates to double-ended wire guides for use in a percutaneous procedure within a body cavity and to methods of using such devices. In certain embodiments, the wire guide includes a break-away discontinuity near at least one end of the wire guide.

18 Claims, 5 Drawing Sheets

(56) References Cited

U.S. PATENT DOCUMENTS

| | | | |
|---|---|---|---|
| 7,621,880 B2* | 11/2009 | Ryan | A61M 25/09 600/585 |
| 7,731,669 B2 | 6/2010 | Matthews et al. | |
| 7,758,565 B2 | 7/2010 | Melsheimer | |
| 7,785,274 B2 | 8/2010 | Mishima et al. | |
| 8,298,160 B2 | 10/2012 | Oslund et al. | |
| 2002/0058888 A1* | 5/2002 | Biagtan | A61M 25/09 600/585 |
| 2002/0133092 A1* | 9/2002 | Oslund | A61M 25/09 600/585 |
| 2004/0225233 A1 | 11/2004 | Frankowski et al. | |
| 2005/0197597 A1 | 9/2005 | Douk | |
| 2008/0064988 A1 | 3/2008 | Carter et al. | |
| 2010/0318001 A1 | 12/2010 | Miyata et al. | |
| 2012/0035707 A1* | 2/2012 | Mitelberg | A61F 2/95 623/1.12 |
| 2013/0204163 A1* | 8/2013 | Simpson | C22C 19/055 600/585 |

* cited by examiner

DOUBLE-ENDED WIRE GUIDE AND METHOD OF USE THEREOF

RELATED APPLICATIONS

This patent application claims the benefit of U.S. provisional patent application No. 62/037,757, filed Aug. 15, 2014, the entire contents of which are hereby incorporated by reference.

TECHNICAL FIELD

The present invention generally relates to double-ended wire guides for use in percutaneous procedures within a body cavity and to methods of using such devices. In certain embodiments, the wire guides include a break-away discontinuity located near one end of the wire guide. In other embodiments, a break-away discontinuity is located near both ends of the wire guide.

BACKGROUND

Wire guides are commonly used in procedures, such as angioplasty procedures, diagnostic and interventional procedures, percutaneous access procedures, or radiological and neuroradiological procedures in general, to introduce a wide variety of medical devices into the vascular system or into other vessels of a human or veterinary patient. For example, wire guides are used for advancing intraluminal devices such as stent delivery catheters, balloon dilation catheters, atherectomy catheters, and the like within body lumens.

Typically, the wire guide is positioned inside the inner lumen of an introducer catheter. The wire guide is advanced out of the distal end of the introducer catheter into the patient until the distal end of the wire guide reaches the location where the interventional procedure is to be performed. After the wire guide is inserted, another device such as a stent and stent delivery catheter is advanced over the previously introduced wire guide into the patient until the stent delivery catheter is in the desired location. After the stent has been delivered, the stent delivery catheter can then be removed from a patient by retracting the stent delivery catheter back over the wire guide. The wire guide may be left in place after the procedure is completed to ensure easy access if it is required.

Wire guides are used extensively and are available in a wide variety of sizes and shapes. Because wire guides are so useful, it may be necessary to purchase and store a great many varieties in order to meet the needs of users. For example, wire guides having differing stiffness may be required for different procedures. This requires that hospitals and other users to purchase, store, and inventory a great many varieties of wire guides to meet all situations and needs that may arise.

BRIEF SUMMARY

One aspect of the present invention provides a wire guide including an elongated member extending from a first end to a second end. In one embodiment, the elongated member is at least 300 cm in length. In another embodiment the elongated member includes a break-away discontinuity positioned within 20 cm of the first end. A second break-away discontinuity may be positioned within 20 cm of the second end. In other embodiments, at least one end of the elongated member is a tapered end. In yet other embodiments, at least one end of the elongated member includes a coil.

The break-away discontinuity can be of any construction providing a preferred breaking point in the elongated member. In various embodiments, the break-away discontinuity is a break-away neck, a partial cut, a heat-treated weakened region, a chemically treated weakened region, a hole in the elongated member, a notch in the elongated member, a geometrically induced stress concentration or a localized reduced diameter portion of the elongated member.

The elongated member can include a material such as stainless steel, a stainless steel alloy, a nickel-titanium alloy, gold, silver, tungsten, palladium, platinum, a cobalt-chromium alloy, iridium or combinations of one or more of these materials. The tapered end may include a polymer jacket covering at least a portion of the taper and may also include a hydrophilic coating on the polymer jacket. In some embodiments, the polymer jacket is a polyurethane jacket. The polymer jacket can include an echogenic material, such as tungsten.

Another aspect of the present invention provides a method of treating an occlusion in a body lumen of a patient. In one embodiment, the method includes advancing a first end of a wire guide as disclosed herein through the body lumen of the patient from a first percutaneous entry point at a first region of the body lumen to a first side of the occlusion, where the occlusion is positioned between the first region of the body lumen and a second region of the body lumen. In this embodiment, the first end includes a break-away discontinuity as disclosed herein.

The first end is then advanced through the occlusion to a second side of the occlusion, through a second percutaneous entry point positioned within the second region of the body lumen, and out of the body lumen. A portion of the first end extending outside the second percutaneous entry point is then removed at the break-away discontinuity to expose a modified terminal end of the wire guide.

In certain embodiments, the advancing of the first end of the wire guide through the second percutaneous entry point and out of the body lumen is performed by advancing a wire guide engagement and withdrawal tool through the body lumen from the second percutaneous entry point to the first end of the wire guide and engaging the first end of the wire guide to the wire guide engagement and withdrawal tool. The engagement and withdrawal tool is then removed through the second percutaneous entry point while engaged with the first end of the wire guide, whereby the first end of the wire guide is removed from the body lumen. In some embodiments, engaging the first end of the wire guide to the withdrawal tool includes receiving the first end of the wire guide within a spatial envelope defined by the wire guide engagement and withdrawal tool and tightening the tool to engage the wire guide.

The body lumen may be an artery. For example, the artery may be an artery of the leg. In some embodiments, the first percutaneous entry point is located below the patient's knee and the second percutaneous entry point is located above the patient's knee. The method may further include loading a medical device onto the modified terminal end of the wire guide. For example, the medical device may be a catheter, a stent, a stent graft or a balloon.

DETAILED DESCRIPTION

Figure 1:
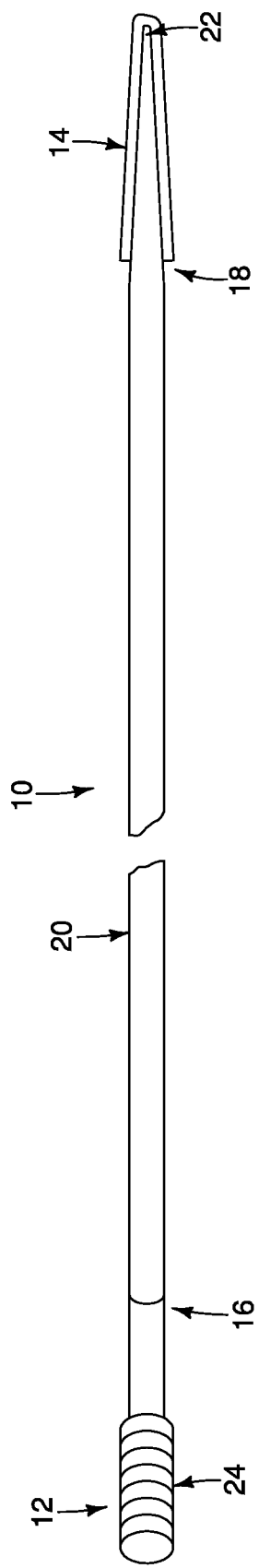
FIG. 1 is an illustration showing one embodiment of a double-ended wire guide.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Each disclosed feature or features can be combined with the generalized features discussed herein, to form a disclosed embodiment of the present invention.

One aspect of the present invention provides a double-ended wire guide having at least one detachable end. Such a double-ended wire guide allows either end of the wire guide, or both ends sequentially, to be inserted into a body lumen of a human or veterinary patient. The body lumen may, for example, be a passage of the vascular system, the alimentary system, the urogenital system or the biliary system. In certain embodiments, the body lumen is a vessel of the peripheral vascular system. In a preferred embodiment, the body lumen is an artery of the leg.

The ends of the wire guide can have different characteristics. For example, the ends of the wire guide may possess differing stiffness, or may differ in their shape or in their hydrophilic properties. Such double-ended wire guides can allow for the reduction of inventory requirements of wire guides. In certain embodiments, one or both ends of the wire guided can include a coiled tip having one or more coils. Differences in the stiffness of such coils can allow for a variation of stiffness of the ends of the wire guide. In other embodiments, one or both ends of the wire guide may be tapered or have a reduced thickness compared to the middle portion of the wire guide. In certain embodiments, one or both ends of the wire guide are detachable from the reminder of the wire guide. A break-away discontinuity is positioned near at least one end of the wire guide and profies a preferred break point, allowing an end of the wire guide to be separated at a defined position.

Referring now to the drawings, there is illustrated in FIG. 1, one embodiment of such a double-ended wire guide. Wire guide 10 includes elongated member 20 having a first end region 12 and a second end region 18. In the embodiment illustrated in FIG. 1, first end region 12 includes chronic total occlusion (CTO) coiled tip 24 having a designated tip load. In certain embodiments, coiled tip 24 includes a stainless steel and/or a palladium coil. FIG. 1 also illustrates second end region 18 including tapered end 22, which, in certain embodiments, is covered by polymer jacket and/or hydrophilic coating 14. In some embodiments, tapered end 22 is covered by a polymer jacket, a surface of which is covered by a hydrophilic coating.

The central portion of elongated member 20, i.e. the portion between first end region 12 and a second end region 18, can have a constant stiffness or can vary in stiffness along its length. For example, the portion of elongated member 20 between first end region 12 and the center of the wire guide can have a stiffness that differs from the portion of elongated member 20 between second end region 18 and the center of the wire guide. This can be achieved by, for example, forming these two portions with differing cross sectional dimensions or from different materials.

In certain embodiments, the elongated member 20 includes a material such as stainless steel, a stainless steel alloy, platinum, palladium, gold, a superelastic nickel-titanium alloy (for example, NITINOL) or combinations thereof. A radiopaque material, such as platinum or gold, is included as part of the elongated member 20 to allow for better visibility during manipulation of the wire guide within the body of the patient. In other embodiments, an echogenic material, such as tungsten, may be included as part of the elongated member 20.

The outside diameter of elongated member 20 can be between, for example 0.010 and 0.03 inches, or between 0.015 and 0.025 inches or between 0.025 and 0.020 inches. Elongated member 20 may have typical wire guide dimensions. In certain embodiments, elongated member 20 is between 90 and 400 cm in length. In other embodiments, elongated member 20 is between 280 and 400 cm in length. In yet other embodiments, elongated member 20 is between 300 and 400 cm in length or is at least 300 cm in length.

FIG. 1 illustrates wire guide 10 including a first break-away discontinuity 16, which is positioned towards first end region 12. The present embodiments also include those in which the first break-away discontinuity is positioned towards second end region 22. First break-away discontinuity 16 is typically positioned within 40 cm, or 30 cm, or 20 cm or 10 cm from the end of elongated member 20.

First break-away discontinuity 16 can be of any construction providing a preferred breaking point in elongated member 20. In various embodiments, the break-away discontinuity is a break-away neck, a partial cut, a heat-treated weakened region, a chemically treated weakened region, a hole in the elongated member, a notch in the elongated member, a geometrically induced stress concentration or a localized reduced diameter portion of elongated member 20.

Figure 2:
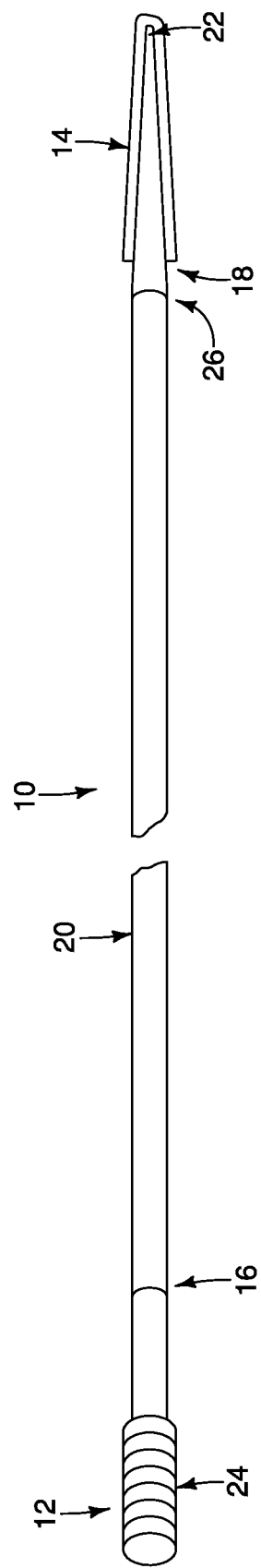
FIG. 2 is an illustration another embodiment of a double-ended wire guide.

FIG. 2 illustrates another embodiment of the present invention. This embodiment includes, in addition to first break-away discontinuity 16, second break-away discontinuity 26. Second break-away discontinuity 26 is typically positioned within 40 cm, or 30 cm, or 20 cm or 10 cm from the second end of elongated member 20.

Another aspect of the present invention provides a method of treating an occlusion in a body lumen of a human or veterinary patient. In various embodiments, the occlusion is a blockage or a partial blockage of the vascular system, the alimentary system, the urogenital system or the biliary system. In certain embodiments, the occlusion is a blockage or a partial blockage of a vessel of the peripheral vascular system, for example, an occlusion of an artery of the leg of a human patient. Such an occlusion may result from peripheral vascular disease, for example atherosclerosis, inflammatory processes leading to stenosis, an embolism, or thrombus formation.

An occlusion of a vascular vessel may also reoccur after angioplasty and related procedures performed to aid in alleviating occlusions. The cause of these recurring obstructions, termed restenosis, may be due to the body responding to the surgical procedure. Restenosis of the vessel may develop over several months after the procedure, and may require another angioplasty procedure to treat the obstruction. Proliferation and migration of smooth muscle cells (SMC) from the media layer of the lumen to the intimal layer cause an excessive production of extracellular matrix (ECM), which is believed to be one of the leading contributors to the development of restenosis. The extensive thickening of tissues narrows the lumen of the blood vessel, constricting or blocking the blood flow through the vessel.

Figure 3:
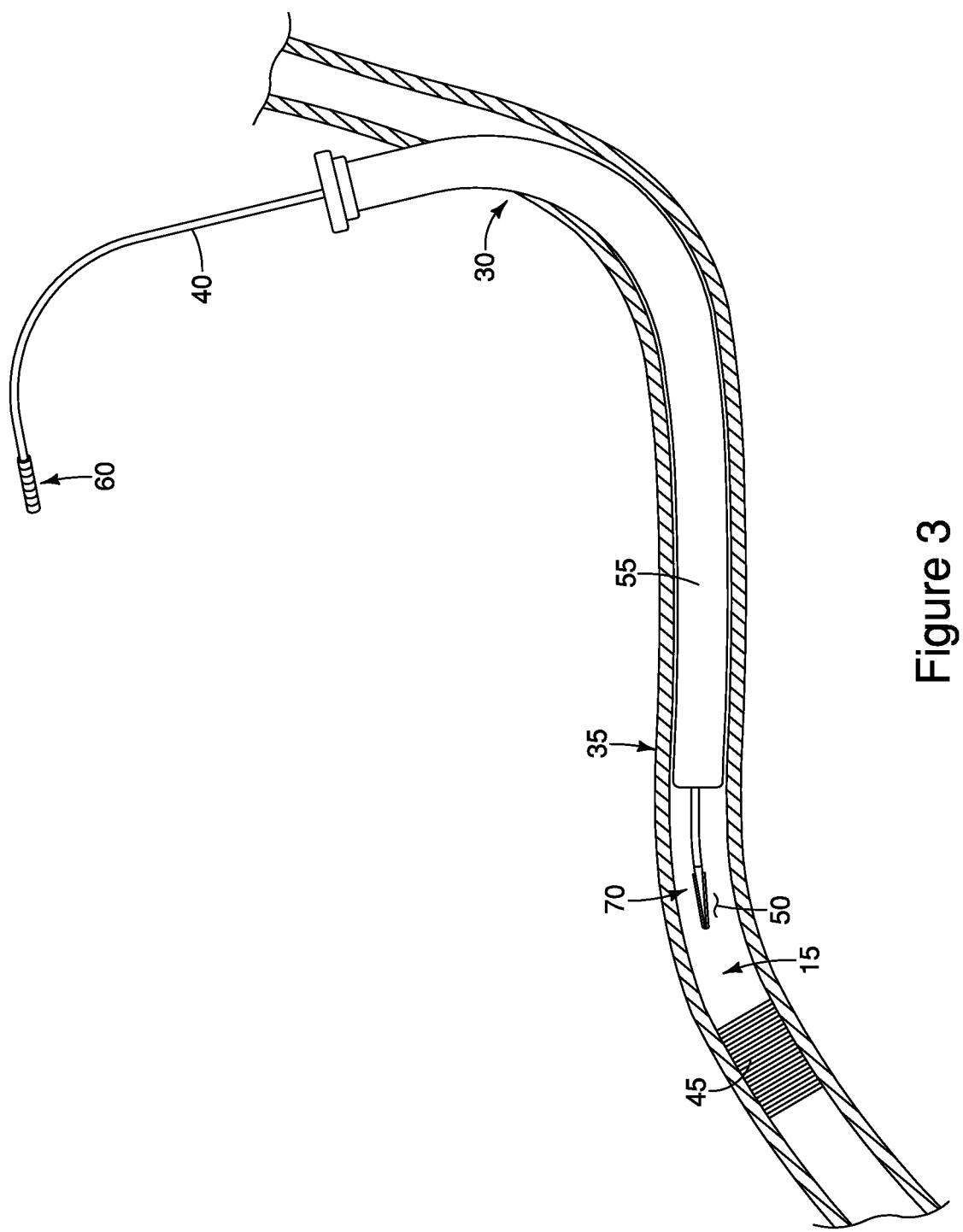
FIG. 3 is an illustration showing a partial cross-sectional view of one stage of a method including the use of one embodiment of a double-ended wire guide.
Figure 4:
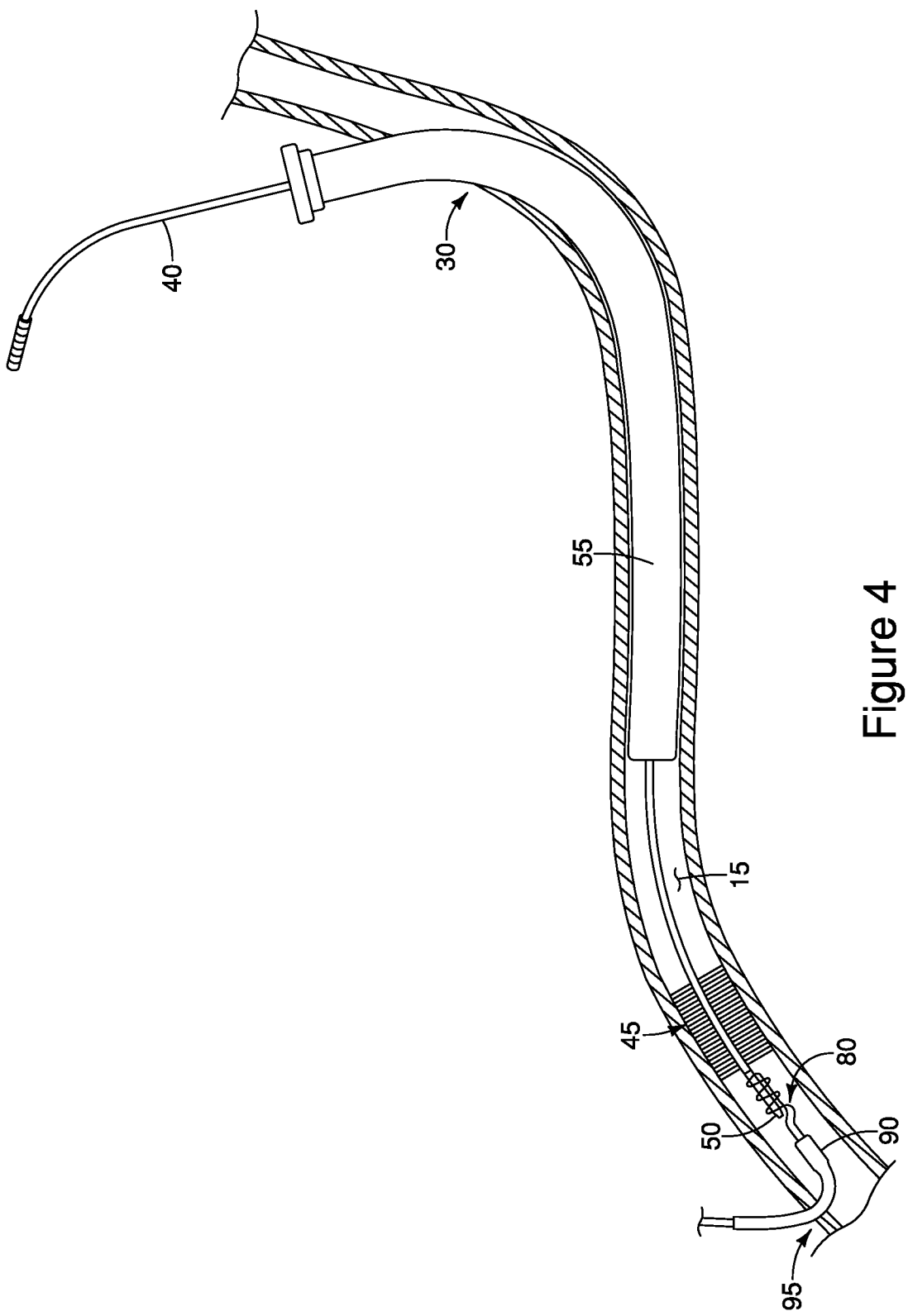
FIG. 4 is an illustration showing a partial cross-sectional view of another stage of a method including the use of one embodiment of a double-ended wire guide.
Figure 5:
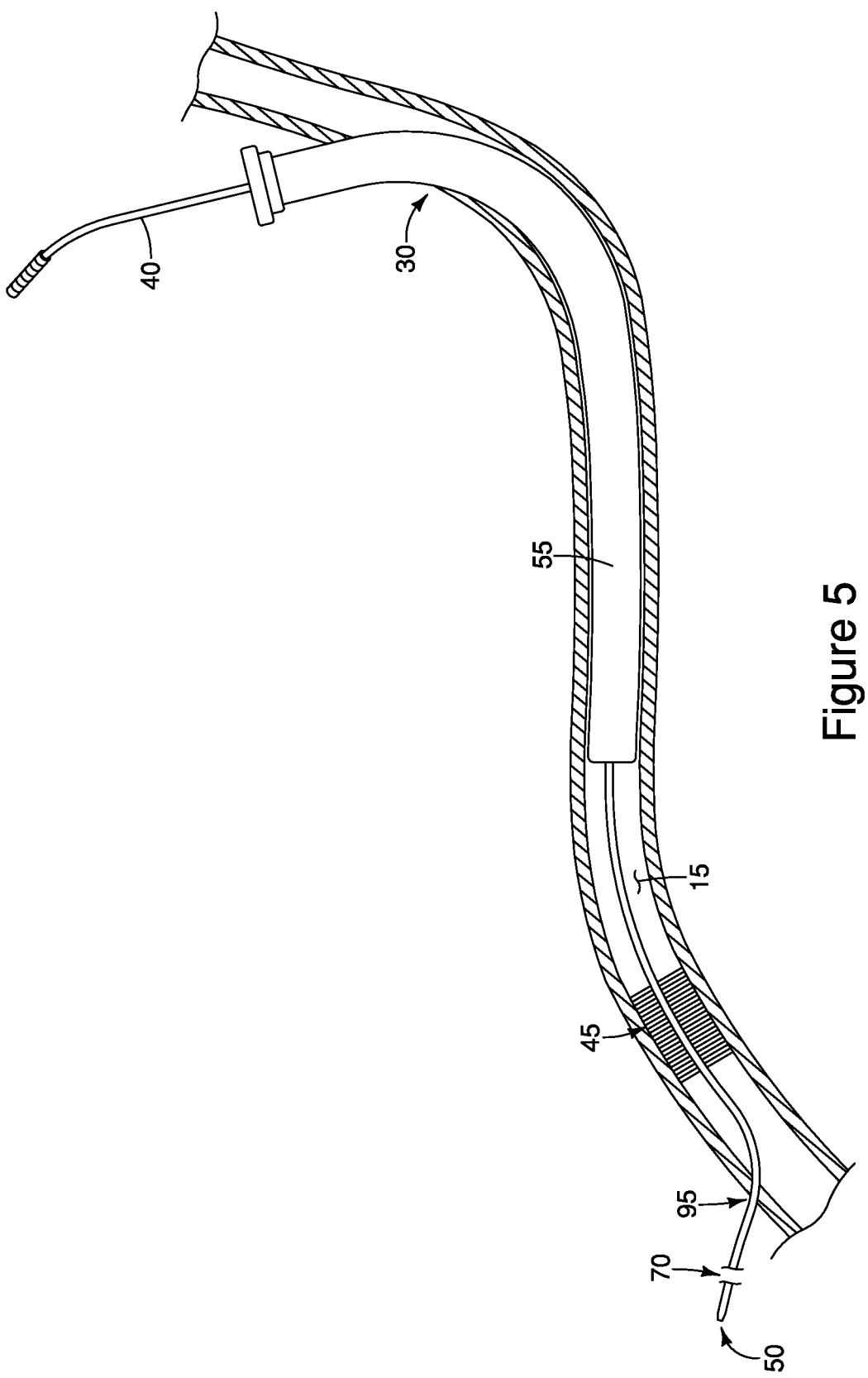
FIG. 5 is an illustration showing a partial cross-sectional view of yet another stage of a method including the use of one embodiment of a double-ended wire guide.

Referring now to FIGS. 3, 4 and 5, these figures illustrate one embodiment of the method of treating such an occlusion. The method includes introducing the wire guide 40 into the occluded vessel 35 of the patient as a first percutaneous entry point 30 positioned at a first region of the body lumen. In one embodiment, the wire guide 40 is introduced at the first percutaneous entry point 30 through the sheath 55.

First end 50 of wire guide 40 is then advanced through body lumen 15 of vessel 35 to a first side of an occlusion 45, through occlusion 45 and is subsequently passed out of body lumen 15 through a second percutaneous entry point 95. In some embodiments, first end 50 is passed through second percutaneous entry point 95 by pushing the portion of wire guide 40 which remains outside a first percutaneous entry point 30 until first end 50 exits body lumen 15. In other embodiments, a wire guide retrieval device is passed into body lumen 15 through second percutaneous entry point 95 and used to engage first end 50 of wire guide 40. The device is then used to pull first end 50 through second percutaneous entry point 95 and out of body lumen 15.

FIG. 4 illustrates the distal end of a wire guide engagement and withdrawal tool that can be used to pull first end 50 out of body lumen 15. Further details of the construction of one embodiment of such a tool are disclosed in co-pending patent application Ser. No. 14/369,746, filed Jun. 30, 2014, entitled "Wire Guide Engagement and Withdrawal Tool and Method", the contents of which are incorporated by reference. The distal end of the tool includes elongated body 90 and gripping portion 80. In one embodiment, the distal end to the tool is inserted through second percutaneous entry point 95 and gripping portion 80 is engaged to the first end of the wire guide. For example, such an engagement may be achieved by first receiving the first end of the wire guide within a spatial envelope defined by the tool and tightening the tool to engage the wire guide. The tool is then withdrawn from the patient lumen through the second percutaneous entry point 95 while engaged with the first end of the wire guide, until the wire guide extends out of the patient at the second percutaneous entry point. A portion of the first end of the wire guide extending outside the second percutaneous entry point can then be removed to expose a modified terminal end of the wire guide. Such a removal can be achieved by breaking the wire guide at break-away discontinuity 70.

The present method allows for the removal of an end of the wire guide if the end is damaged during, for example, passage through the occlusion, during the snaring process or during the passage out of the lumen. Such damage can make it difficult or impossible for a medical device, such as a stent or balloon to be loaded onto the wire guide. Removal of the damaged end avoids such difficulty and allows the loading of such devices, which may then be then utilized during a subsequent stage of the treatment procedure.

In one embodiment, the present method can be used in an angioplasty, stenting and other technique practice for treating an obstructed vessel within the human anatomy. For example, the method can be used for the treatment of an obstructed artery in the leg. In such a technique, a wire guide is first introduced into the artery having the obstruction. Normally, during such a procedure, the wire guide is introduced through a puncture in the groin region of the patient into a region upstream (antegrade) of the obstruction. The wire guide is then advanced into the artery and through the obstruction. However, depending on the nature and severity of the obstruction, it may not be possible to achieve passage through the obstruction from an antegrade direction.

For example, the external anatomy of the patient may not be conducive to this type of technique. Moreover, force transmission through the wire guide and steering may be difficult, especially if the obstruction is far removed from the entry point. In addition, should the diseased vessel have a total occlusion, the antegrade side of the obstruction can be calcified and especially difficult to puncture from this direction.

The present method provides a technique for crossing such challenging obstructions by accessing the obstructed vessel from a down-stream (retrograde) direction. Depending on the site of the obstruction, the wire guide may be introduced through an entry point that is below the knee, for example, in the region of the ankle or foot, and then advanced through the obstruction from a down-stream direction. A wire guide introduced in this manner can be more effective in puncturing the fibrous cap and may be able to be introduced at a point that is closer to the obstruction.

The wire guide can then be advanced to a second entry point, usually in the groin region. Here, the end of the wire guide can be either pushed through the second entry point, or snared as disclosed herein, and removed from the artery. If the tip of the wire guide is damaged, the tip can then be removed by breaking the end of the wire guide at break-away discontinuity. A stent, balloon or other device can then be inserted over the wire guide and advanced to the region of the obstruction to continue treatment of the obstruction. In one embodiment, such a procedure allows for entry of the device through larger diameter vessels of the body, for example of the upper leg.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

We claim:

1. A wire guide comprising:
   an elongated member adapted to insert a medical device into a patient, the elongated member having a length extending continuously between a first end to a second end, wherein the elongated member is between 90 and 400 cm in length and wherein the elongated member comprises a first break-away discontinuity positioned within 20 cm of the first end and a second break-away discontinuity positioned within 20 cm of the second end, wherein the second end comprises a taper; and
   wherein the first end comprises a coil, wherein both of the break-away discontinuities comprise defined positions along the length of the elongated member at which the first and second ends of the elongated member are in breakable communication with the rest of the length of the elongated member, wherein the first break-away discontinuity allows for irreversible removal of the first end of the elongated member and the second break-away discontinuity allows for irreversible removal of the second end of the elongated member, and wherein the break-away discontinuities are configured to be broken to remove a portion of the length of the elongated member defining its first or second end and expose a modified first or second end.

2. The wire guide of claim 1, wherein at least one of the first break-away discontinuity and the second break-away discontinuity comprises a discontinuity selected from the group consisting of a break-away-neck, a partial cut, a heat-treated weakened region, a chemically treated weakened region and a hole in the elongated member.

3. The wire guide of claim 1, wherein the elongated member comprises a material selected from the group consisting of stainless steel, a nickel-titanium alloy, gold, silver, tungsten, palladium, platinum, a cobalt-chromium alloy, iridium, and combinations thereof.

4. The wire guide of claim 1, further comprising a polymer jacket covering at least a portion of the taper and a hydrophilic coating on the polymer jacket.

5. The wire guide of claim 1 wherein the modified terminal end of the elongated member is adapted to receive a medical device without further modification.

6. The wire guide of claim 5 wherein the medical device is chosen from the group consisting of a catheter, a stent, a stent graft, a balloon, or a combination thereof.

7. The wire guide as recited in claim 1 wherein the first end and the second end are configured to be removed by hand.

8. The wire guide of claim 1 wherein the first and second ends are adapted for insertion into a body lumen of the patient.

9. A wire guide comprising: an elongated member adapted to insert a medical device into a patient, the elongated member extending continuously along a length from a first end to a second end, wherein the elongated member comprises a first break-away discontinuity positioned proximate to the first end and a second break-away discontinuity positioned intermediate the first break-away discontinuity and the second end, wherein one of the first and second end comprises a taper; and wherein the other of the first end and second end comprises a coil wherein the first break-away discontinuity and the second break-away discontinuity are defined positions along the length of the elongated member at which the first and second ends are in breakable communication with the rest of the length of the elongated member, wherein the first break-away discontinuity allows for irreversible removal of the first end of the elongated member and the second break-away discontinuity allows for irreversible removal of the second end of the elongated member, and wherein the discontinuities are adapted to be broken to remove a portion of the length of the elongated member to expose a modified first or second end of the elongated member; wherein the first break-away discontinuity is positioned a distance away from the first end, the distance selected from the group consisting of 40 cm, 30 cm, 20 cm, and 10 cm; wherein the second break-away discontinuity is positioned a distance away from the first end, the distance selected from the group consisting of 40 cm, 30 cm, 20 cm, and 10 cm.

10. The wire guide of claim 9 wherein the elongated member is between 90 and 400 cm in length.

11. The wire guide of claim 9, wherein at least one of the first break-away discontinuity and the second break-away discontinuity comprises a discontinuity selected from the group consisting of a break-away-neck, a partial cut, a heat-treated weakened region, a chemically treated weakened region and a hole in the elongated member.

12. The wire guide of claim 9, wherein the elongated member comprises a material selected from the group consisting of stainless steel, a nickel-titanium alloy, gold, silver, tungsten, palladium, platinum, a cobalt-chromium alloy, iridium, and combinations thereof.

13. The wire guide of claim 9, further comprising a polymer jacket covering at least a portion of the taper and a hydrophilic coating on the polymer jacket.

14. The wire guide of claim 9 wherein the modified first or second end of the elongated member is adapted to receive a medical device without further modification.

15. The wire guide of claim 14 wherein the medical device is chosen from the group consisting of a catheter, a stent, a stent graft, a balloon, or a combination thereof.

16. The wire guide as recited in claim 9 wherein the first end and the second end are configured to be removed manually.

17. The wire guide of claim 9 wherein the first and second ends are adapted for insertion into a body lumen of the patient.

18. A wire guide comprising: an elongated member adapted to insert a medical device into a patient, the elongated member having a length extending continuously between a first end to a second end, wherein the first and second ends are adapted for insertion into a body lumen of a patient, wherein the elongated member is between 90 and 400 cm in length and wherein the elongated member comprises a first break-away discontinuity positioned within 20 cm of the first end and a second break-away discontinuity positioned within 20 cm of the second end, wherein both of the break-away discontinuities comprise defined positions along the length of the elongated member that are configured to be broken to remove a portion of the length of the elongated member defining its first or second end and expose a modified first or second end; wherein the first break-away discontinuity allows for irreversible removal of the first end of the elongated member and the second break-away discontinuity allows for irreversible removal of the second end of the elongated member.

* * * * *